(12) United States Patent
Lam et al.

(10) Patent No.: US 10,134,132 B2
(45) Date of Patent: *Nov. 20, 2018

(54) SIGNAL PROCESSING FOR INTRAVASCULAR IMAGING

(71) Applicant: ACIST Medical Systems, Inc., Eden Prairie, MN (US)

(72) Inventors: Duc Lam, San Jose, CA (US); J Steve Reynolds, Palo Alto, CA (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/615,130

(22) Filed: Jun. 6, 2017

(65) Prior Publication Data

US 2017/0301089 A1 Oct. 19, 2017

Related U.S. Application Data

(63) Continuation of application No. 14/508,707, filed on Oct. 7, 2014, now Pat. No. 9,704,240.
(Continued)

(51) Int. Cl.
*A61B 5/00* (2006.01)
*G06T 7/00* (2017.01)
(Continued)

(52) U.S. Cl.
CPC .......... *G06T 7/0012* (2013.01); *A61B 5/0066* (2013.01); *A61B 5/02007* (2013.01);
(Continued)

(58) Field of Classification Search
CPC .................................................. A61B 5/0066
See application file for complete search history.

(56) References Cited

U.S. PATENT DOCUMENTS 3,918,025 A * 11/1975 Koshikawa ........... G01S 7/6245
367/102
4,347,443 A 8/1982 Whitney et al.
(Continued)

FOREIGN PATENT DOCUMENTS

CN 101208045 A 6/2008
CN 103025247 A 4/2013
(Continued)

OTHER PUBLICATIONS

Dumane et al., "Use of Frequency Diversity and Nakagami Statistics in Ultrasonic Tissue Characterization," IEEE Transactions on Ultrasonics, Ferroelectrics, and Frequency Control, vol. 48, No. 5, Sep. 2001, pp. 1139-1146.
(Continued)

*Primary Examiner* — Rochelle Turchen
(74) *Attorney, Agent, or Firm* — Fredrikson & Byron, P.A.

(57) ABSTRACT

An intravascular imaging system includes a transducer capable of generating raw data representative of the structure of a patient's vasculature. The system includes an imaging engine for receiving the raw data and generating enhanced data for presentation to a user. The imaging engine includes a coherence filter, an envelope detection module having one or more envelope detectors, and a spatial filter for processing data in various stages. Such stages of processing in the imaging engine act to reduce high frequency noise, generate low frequency data, reduce low frequency noise, and display low frequency data with an improved signal-to-noise ratio. The system can include an image generator for generating an image based on enhanced data and a display for displaying the generated image.

20 Claims, 7 Drawing Sheets

Related U.S. Application Data (60) Provisional application No. 61/887,811, filed on Oct. 7, 2013.

(51) Int. Cl.
| | | |
|---|---|---|
| *A61B 8/12* | (2006.01) | |
| *A61B 8/08* | (2006.01) | |
| *A61B 5/02* | (2006.01) | |
| *G01S 15/89* | (2006.01) | |
| *G01S 7/52* | (2006.01) | |

(52) U.S. Cl.
CPC ............ *A61B 5/742* (2013.01); *A61B 8/0891* (2013.01); *A61B 8/12* (2013.01); *A61B 8/5207* (2013.01); *A61B 8/5269* (2013.01); *G01S 7/52034* (2013.01); *G01S 7/52046* (2013.01); *G01S 7/52077* (2013.01); *G01S 15/8977* (2013.01); *G01S 15/8956* (2013.01); *G06T 2207/30101* (2013.01)

(56) References Cited

U.S. PATENT DOCUMENTS

| | | | |
|---|---|---|---|
| 4,850,363 A | 7/1989 | Yanagawa et al. | |
| 4,860,758 A | 8/1989 | Yanagawa et al. | |
| 4,949,310 A | 8/1990 | Smith et al. | |
| 5,070,734 A | 12/1991 | Kawabuchi et al. | |
| 5,070,735 A | 12/1991 | Reichert et al. | |
| 5,131,396 A | 7/1992 | Ishiguro et al. | |
| 5,183,048 A | 2/1993 | Eberle et al. | |
| 5,203,338 A | 4/1993 | Jang et al. | |
| 5,363,849 A | 11/1994 | Suorsa et al. | |
| 5,396,285 A | 3/1995 | Hedberg et al. | |
| 5,462,057 A | 10/1995 | Hunt et al. | |
| 5,531,679 A | 7/1996 | Schulman et al. | |
| 5,741,552 A | 4/1998 | Takayama et al. | |
| 5,833,615 A | 11/1998 | Wu et al. | |
| 5,848,969 A | 12/1998 | Panescu et al. | |
| 5,876,343 A | 3/1999 | Teo et al. | |
| 5,921,931 A | 7/1999 | O'Donnell et al. | |
| 6,015,385 A | 1/2000 | Finger et al. | |
| 6,036,650 A | 3/2000 | Wu et al. | |
| 6,132,374 A | 10/2000 | Hossack et al. | |
| 6,139,501 A | 10/2000 | Roundhill et al. | |
| 6,154,572 A | 11/2000 | Chaddha et al. | |
| 6,216,025 B1 | 4/2001 | Kruger | |
| 6,589,181 B2 | 7/2003 | Grunwald et al. | |
| 6,645,147 B1 | 11/2003 | Jackson et al. | |
| 7,194,294 B2 | 3/2007 | Panescu et al. | |
| 7,691,061 B2 | 4/2010 | Hirota | |
| 7,925,064 B2 | 4/2011 | Cloutier et al. | |
| 2001/0017941 A1 | 8/2001 | Chaddha | |
| 2001/0029336 A1 | 10/2001 | Teo | |
| 2003/0063787 A1 | 4/2003 | Natanzon et al. | |
| 2003/0078497 A1 | 4/2003 | Ji et al. | |
| 2003/0097069 A1 | 5/2003 | Avinash et al. | |
| 2003/0208123 A1 | 11/2003 | Panescu | |
| 2004/0030250 A1 | 2/2004 | Stewart | |
| 2004/0037164 A1 | 2/2004 | Garlick et al. | |
| 2004/0199047 A1 | 10/2004 | Taimisto et al. | |
| 2005/0215897 A1 | 9/2005 | Sakaguchi et al. | |
| 2006/0253028 A1 | 11/2006 | Lam et al. | |
| 2007/0016068 A1 | 1/2007 | Grunwald et al. | |
| 2007/0167710 A1 | 7/2007 | Unal et al. | |
| 2008/0015569 A1 | 1/2008 | Saadat et al. | |
| 2008/0031498 A1 | 2/2008 | Corcoran et al. | |
| 2008/0200815 A1 | 8/2008 | Van Der Steen et al. | |
| 2008/0234582 A1 | 9/2008 | Nair et al. | |
| 2009/0088830 A1 | 4/2009 | Mohamed et al. | |
| 2009/0284332 A1 | 11/2009 | Moore et al. | |
| 2010/0010344 A1 | 1/2010 | Ahn et al. | |
| 2010/0094127 A1 | 4/2010 | Xu | |
| 2010/0174190 A1 | 7/2010 | Hancock et al. | |
| 2010/0312092 A1 | 12/2010 | Maurice et al. | |
| 2010/0312109 A1 | 12/2010 | Satoh | |
| 2011/0071404 A1 | 3/2011 | Schmitt et al. | |
| 2011/0087104 A1* | 4/2011 | Moore ..................... A61B 8/12 600/447 |
| 2011/0160586 A1 | 6/2011 | Li et al. | |
| 2012/0123271 A1 | 5/2012 | Cai | |
| 2012/0170848 A1 | 7/2012 | Kemp et al. | |
| 2013/0109968 A1 | 5/2013 | Azuma | |
| 2013/0317359 A1 | 11/2013 | Wilson et al. | |
| 2014/0180078 A1 | 6/2014 | Nair | |
| 2014/0268167 A1 | 9/2014 | Friedman et al. | |
| 2014/0276065 A1 | 9/2014 | He et al. | |
| 2014/0350404 A1 | 11/2014 | Rajguru et al. | |
| 2015/0099975 A1 | 4/2015 | Lam et al. | |
| 2017/0100100 A1 | 4/2017 | Jamello et al. | |
| 2017/0193658 A1 | 7/2017 | Cardinal et al. | |
| 2017/0330331 A1 | 11/2017 | Bhatt et al. | |
| 2018/0042575 A1 | 2/2018 | Moore et al. | |

FOREIGN PATENT DOCUMENTS

| | | |
|---|---|---|
| EP | 346889 A1 | 12/1989 |
| EP | 851241 A2 | 7/1998 |
| EP | 1387317 A1 | 2/2004 |
| EP | 1988505 A1 | 11/2008 |
| EP | 1609423 B2 | 3/2010 |
| EP | 2488107 A2 | 8/2012 |
| JP | 62221335 A | 9/1987 |
| JP | H09000522 A | 1/1997 |
| JP | 2001333902 A | 12/2001 |
| JP | 2002530143 A | 9/2002 |
| JP | 2004180784 A | 7/2004 |
| JP | 2006014938 A | 1/2006 |
| JP | 2007029520 A | 2/2007 |
| JP | 2007229015 A | 9/2007 |
| JP | 2008508970 A | 3/2008 |
| JP | 2008536638 A | 9/2008 |
| JP | 2009545406 A | 12/2009 |
| JP | 4648652 B2 | 3/2011 |
| JP | 2013507227 A | 3/2013 |
| WO | 0101864 A1 | 1/2001 |
| WO | 2006015877 A1 | 2/2006 |
| WO | 2006113857 A1 | 10/2006 |
| WO | 2006122001 A2 | 11/2006 |
| WO | 2007098209 A2 | 8/2007 |
| WO | 2008016992 A1 | 2/2008 |
| WO | 2011046903 A2 | 4/2011 |
| WO | 2014186268 A1 | 11/2014 |
| WO | 2017062265 A1 | 4/2017 |
| WO | 2017100274 A1 | 6/2017 |

OTHER PUBLICATIONS

Foster, "Transducer Materials and Probe Construction," Ultrasound in Medicine and Biology, vol. 26, Supp. 1, 2000, pp. S2-S5.

Frijlink et al., "High Frequency Harmonic Imaging in Presence of Intravascular Stents," IEEE Ultrasonics Symposium, 2003, pp. 208-211.

Garcia-Garcia et al., "Imaging of coronary atherosclerosis: intravascular ultrasound," European Heart Journal, vol. 3, 2010, pp. 2456-2469.

International Patent Application No. PCT/US2014/059467, International Search Report & Written Opinion dated Dec. 18, 2014, 11 pages.

International Patent Application No. PCT/US2014/059467, International Preliminary Report on Patentability dated Jan. 15, 2016, 28 pages.

Seo et al., "Sidelobe Suppression in Ultrasound Imaging Using Dual Apodization with Cross-Correlation," IEEE Transactions on Ultrasonics, Ferroelectrics, and Frequency Control, vol. 55, No. 10, Oct. 2008, pp. 2198-2210.

Shankar et al., "Computer-Aided Classification of Breast Masses in Ultrasonic B-Scans Using a Multiparameter Approach," IEEE Transactions on Ultrasonics, Ferroelectrics, and Frequency Control, vol. 50, No. 8, Aug. 2003, pp. 1002-1009.

Smith et al., "The Maltese Cross Processor: Speckle Reduction for Circular Transducers," Ultrasonic Imaging, vol. 10, No. 3, Jul. 1988, pp. 153-170.

(56) References Cited

OTHER PUBLICATIONS

U.S. Appl. No. 61/218,177, titled Vector Domain Image Enhancement for Mechanically Rotating Imaging Catheters, filed Jun. 18, 2009.
Van Der Steen et al., "IVUS Harmonic Imaging," Ultrasound in Medicine and Biology, vol. 26, Supp. 2, 2000, p. A90.
Wang et al., "Optimizing the Beam Pattern of a Forward-Viewing Ring-Annular Ultrasound Array for Intravascular Imaging," IEEE Transactions on Ultrasonics, Ferroelectrics, and Frequency Control, vol. 49, No. 12, Dec. 2002, pp. 1652-1664.
Waters et al., "Development of a High-Definition Intravascular Ultrasound Imaging System and Catheter," IEEE International Ultrasonics Symposium Proceedings, Oct. 18, 2011, 4 pages.
Moore et al., "Intravascular Ultrasound Image Processing of Blood-Filled or Blood-Displaced Lumens," U.S. Appl. No. 15/704,710, filed Sep. 14, 2017, 49 pages.

\* cited by examiner

SIGNAL PROCESSING FOR INTRAVASCULAR IMAGING

TECHNICAL FIELD

This disclosure is related to the field of intravascular imaging and processing of intravascular image data.

BACKGROUND

Intravascular imaging is often used to identify diagnostically significant characteristics of a vessel. For example, an intravascular imaging system may be used by a healthcare professional to help identify and locate blockages or lesions in a vessel. Common intravascular imaging systems include intravascular ultrasound (IVUS) systems as well as optical coherence tomography (OCT) systems.

IVUS systems include one or more ultrasound transducers emitting ultrasound energy based on received electrical signals and sending return electrical signals based on ultrasound energy reflected by various intravascular structures. In some instances, a console with a high-resolution display is able to display IVUS images in real-time. In this way, IVUS can be used to provide in-vivo visualization of the vascular structures and lumens, including the coronary artery lumen, coronary artery wall morphology, and devices, such as stents, at or near the surface of the coronary artery wall. IVUS imaging may be used to visualize diseased vessels, including coronary artery disease. In some instances, the ultrasound transducer(s) can operate at a relatively high frequency (e.g., 10 MHz-60 MHz, in some preferred embodiments, 40 MHz-60 MHz) and can be carried near a distal end of an IVUS catheter assembly. Some IVUS systems involve 360-degree visualization of the vessel (e.g., mechanically rotating the IVUS catheter assembly, steering IVUS signals from phased-array transducers, etc.).

Electrical signals received by the transducer can be in the form of image information and can be used to construct images. In some systems, analog image information can be digitized into vector form. An image can then be constructed from a series of vectors. For example, M vectors each comprising N data points can be used to construct an M×N two-dimensional image. In some systems, images of vascular structures of a patient can be generated and displayed real-time to provide in-vivo visualization of such structures.

The transducer typically produces analog signals and operates at a particular frequency. Generally, the resolution of the image information received increases with the operating frequency of the transducer and the frequency of data acquisition from the transducer. That is, high frequency images tend to have better resolution than low frequency images. However, data acquired at a high frequency often includes greater signal loss, and thus a lower signal to noise ratio ("SNR") when compared to low frequency images because of losses associated with high frequency transmission. This can result in dark, hard-to-see images or very noisy images if the image intensity is amplified via increased gain. As a result, most intravascular imaging is performed at a relatively low frequency, sacrificing image resolution for an improved SNR.

In some systems, image information is processed to improve the SNR. Processing can include combining data such as averaging, envelope detection, and/or selecting various data points to eliminate, such as outlier elimination. However, each processing step takes time. For example, in some systems, envelope detection can require each vector to be passed through the envelope detector one-by-one, slowing down the imaging process. If the processing delay is too long, it can become impossible to generate a real-time display for in-vivo visualization of the vascular structures being imaged.

SUMMARY

Embodiments of the present invention provide an intravascular imaging system with high frequency image information acquisition and effective noise filtering of the entire range of noise. Processing steps are performed to achieve high resolution, low noise images. Low enough degree of noise permits the image information to be amplified to show high resolution detail without also amplifying the noise to a point at which it obscures the image.

In some embodiments, such processing steps can include coherence filtering of high frequency data, envelope detection to convert the high frequency data to low frequency data, and spatial filtering of low frequency data. Some processes such as envelope detection can be performed in parallel to expedite processing. In some embodiments, processing steps are performed quickly enough to generate and display a high resolution image from high frequency image information in real time.

Systems for performing such measurements can include an intravascular imaging catheter assembly configured to generate a raw frame of imaging information corresponding to its surroundings during data collection, for example, a patient's vasculature. The raw frame of imaging information can include a raw set of vectors, each vector in the raw set of vectors including a raw set of data points. In some instances, each vector is representative of an angular portion of image information, while each data point within the vector is representative of a radial dimension along that angular portion. The system can include an imaging engine for receiving the raw frame of imaging information from the intravascular imaging catheter assembly and producing an enhanced frame of imaging information that includes an enhanced set of vectors.

The imaging engine can include a coherence filter configured to group vectors from the raw set of vectors into raw vector groups and to generate a first set of vectors based on comparisons of data points within the raw vector groups. In some cases, the comparisons are between points of like radial position within each vector. Vectors in the first set of vectors are each generally representative of the vectors in one of the raw vector groups and include a first set of data points. The first set of data points within each vector in the first set of vectors can include the same number of data points as each set of raw data points in the raw imaging information.

The imaging engine can include an envelope detection module for receiving the first set of vectors and generating a second set of vectors based on comparisons of data points within each first set of data points with one another. Each vector in the second set of vectors can include a second set of data points. Each second set of data points can have a smaller number of data points than its associated first set, but can be representative of the first set of data points. In some cases, the second set of data points can include a lower-frequency representation of the first set of data points. The second set of vectors can include the same number of vectors as the first set.

The imaging engine can include a spatial filter for receiving the second set of vectors and generating an enhanced set of vectors. The spatial filter can group vectors from the second set of vectors into processed vector groups, and generate an enhanced set of vectors based on comparisons of data points of each processed vector group. The spatial filter can include comparisons of data points within each processed vector group having like and near radial position. In some examples, each processed vector group can be used to generate a single enhanced vector in the set of vectors. Each enhanced vector can include the same number of data points as the second set of data points in associated vectors in the second set of vectors. The enhanced set of vectors can be combined to produce the enhanced frame of imaging information.

In some systems, the imaging engine can include an image generator configured to generate an image based on the enhanced frame of imaging information. Such systems can include a display coupled to the imaging engine for displaying images generated by the image generator. In some systems, images can be displayed to a user in substantially real time from the image generator and display.

DETAILED DESCRIPTION

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
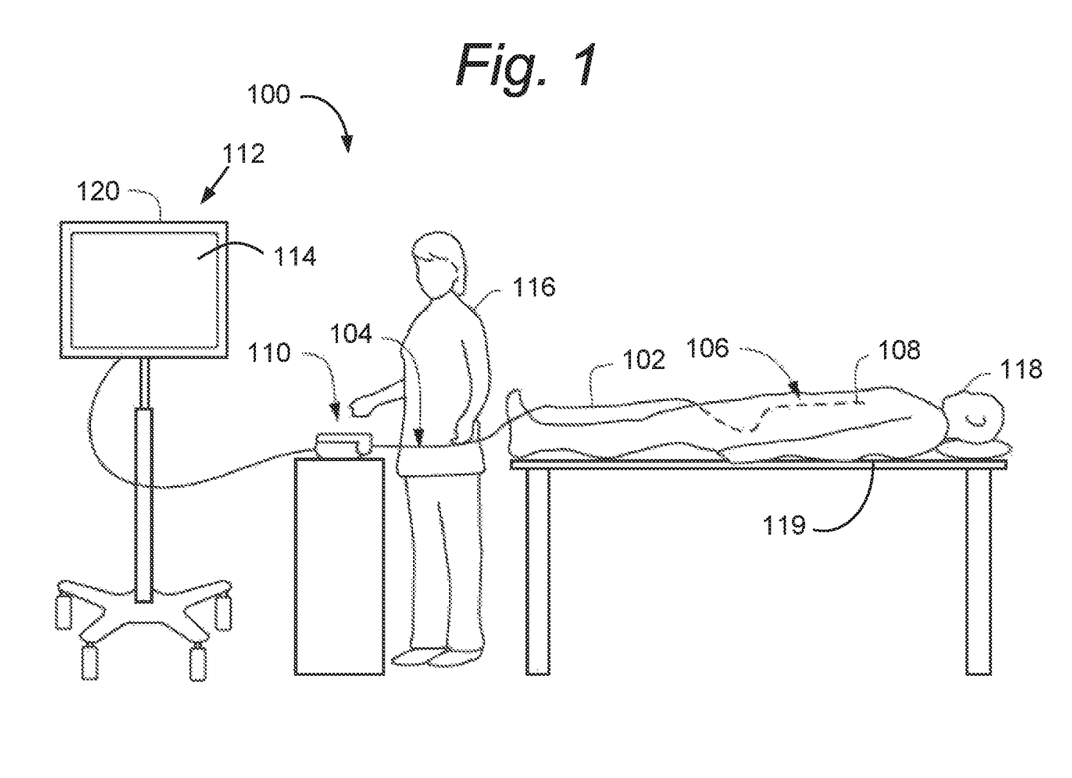
FIG. 1 is an illustrative embodiment of an intravascular imaging system.

FIG. 1 is an illustrative example of a system 100 that may be configured to perform intravascular imaging. System 100 may include a catheter assembly 102, a translation mechanism 110, and a user interface 120. The catheter assembly 102 may include a proximal end 104 and a distal end 106 configured to be inserted into a vessel of a patient 118. In one example, catheter assembly 102 may be inserted into the patient 118 via the femoral artery and guided to an area of interest within the patient 118. The broken lines in FIG. 1 represent portions of catheter assembly 102 within the patient 118.

In some examples, catheter assembly 102 may include a transducer 108 within distal end 106 configured to emit and receive wave-based energy and generate imaging data—e.g., to image the area of interest within the patient 118. For example, where system 100 is an IVUS system, transducer 108 may comprise an IVUS imaging probe including an ultrasound transducer configured to emit and receive ultrasound energy and generate ultrasound data. In another example, system 100 may be an OCT system wherein the transducer 108 may comprise an OCT imaging probe configured to emit and receive light and generate OCT data.

In some embodiments, the catheter assembly 102 can include an imaging assembly and a sheath. The imaging assembly can include the transducer 108, a drive cable, and a transmission line (e.g., a coaxial cable). The sheath can define a lumen within which the imaging assembly is allowed to move freely. The drive cable can be fixed to the transducer 108 such that movement of the drive cable through the sheath causes the transducer 108 to move through the sheath as well. Thus, in some embodiments, the transducer 108 can both translate and rotate within the sheath via the drive cable without the sheath moving within the artery. This can be advantageous to avoid excess friction between the catheter assembly 102 and the interior of a patient's artery as the transducer 108 is moved during imaging or other intravascular imaging operations. For example, while moving inside the sheath, the catheter assembly 102 does not drag along vessels which may have plaques prone to rupture.

The intravascular imaging system 100 can include a translation mechanism 110. As shown, the translation mechanism 110 can be mechanically engaged with the catheter assembly 102 and configured to translate the catheter assembly 102 a controlled distance within the patient 118 during a pullback or other translation operation. In some embodiments, the translation mechanism 110 can act as an interface with the catheter assembly 102. The translation mechanism 110 can translate all or part of the catheter assembly 102 through the vasculature of the patient 118. For example, in an embodiment in which the catheter assembly 102 comprises a drive cable attached to the transducer 108 housed within a sheath, the translation mechanism 110 can act to translate the drive cable and transducer 108 through the sheath while keeping the sheath fixed.

The intravascular imaging system 100 can include an intravascular imaging engine 112. In some embodiments, the intravascular imaging engine 112 can include a processor such as a digital signal processor (DSP), an application specific integrated circuit (ASIC), or a field-programmable gate array (FPGA), a user interface 120, memory, a display 114, and so on. The intravascular imaging engine 112 can receive image information from the catheter assembly 102, and in some embodiments, the processor of the intravascular imaging engine 112 can process the image information and/or generate a display based on the image information received from the catheter assembly 102. In various embodiments, the intravascular imaging engine 112 can present the generated display on display 114 and/or store the generated display in memory. In some embodiments, the display 114 can be updated real-time to provide in-vivo visualization of the vasculature of the patient 118.

In some embodiments, the user interface 120 can receive commands by a system user 116 and/or display intravascular imaging data acquired from the catheter assembly 102 (e.g., intravascular images). The user interface 120 may include a traditional PC or PC interface with software configured to communicate with the other components of the intravascular imaging system 100. In some embodiments, the user interface 120 may include the display 114, which may be configured to display system information and/or imaging signals from the catheter assembly 102 (e.g., intravascular images). In some embodiments, the user interface 120 includes a touchscreen display, which can act to both receive commands from a system user 116 and display intravascular imaging data from the catheter assembly 102.

While the intravascular imaging engine 112 can comprise a processor, user interface 120, memory, and a display 114, the intravascular imaging engine 112 can alternatively comprise any combination of these or other components suitable for performing the functions of the intravascular imaging engine 112 disclosed herein. For example, the intravascular imaging engine 112 can comprise a processor configured to receive image information from the catheter assembly 102 and generate a display. In such embodiments, the intravascular imaging engine 112 can be in communication with any of a user interface, a display 114 on which to present the generated display, and/or memory in which to store generated display if any such component is not part of the intravascular imaging engine 112.

In some embodiments, analog image information from the transducer 108 can be digitized into a series of vectors to be digitally processed. In an exemplary embodiment, a single vector can include N data points, each point corresponding to a distance away from the transducer 108. Images can be constructed out of M vectors, each vector corresponding to an orientation of a rotatable transducer 108 (e.g., mechanically rotated, phased array, etc.). On a high level, the M vectors of N data points can be used to construct an image with M×N data points in polar coordinates. In some embodiments, each vector comprises information representing an angular section extending outward from the transducer 108. Because of the angular width of the wave-based energy emitted by the transducer 108, it is common for a portion of the imaged angular section of vasculature from one vector to be included in one or more additional vectors. In other words, imaged angular sections represented by differing vectors can overlap one another in the course of generating M vectors.

In some embodiments, to construct a vector, the imaging engine can sample data from the transducer 108 at a series of points in time (e.g., N points) and populate the vector with each subsequently received data point. Accordingly, the frequency of data collection corresponds to the vector size, N. As discussed elsewhere herein, a higher frequency image generally has higher resolution but with lower signal levels due to more signal loss, or equivalently, a lower SNR when compared to a lower frequency. For example, the transmission line of the catheter assembly 102 can act as an antenna and pick up electrical noise from various sources within the environment in which the intravascular imaging system 100 is operating.

In some preferred embodiments, the intravascular imaging engine 112 can be configured to process image information acquired at a high frequency to effectively improve the SNR. In some embodiments, the intravascular imaging engine 112 receives a set of high frequency image information from the transducer 108, comprising M vectors, with each vector comprising N data points. In some embodiments, the high frequency image information is a raw frame of imaging information including a raw set of vectors, each vector of the raw set of vectors including a raw set of data points. For instance, in various examples, high frequency image information can include a raw set of 4096, 2048, or 1024 vectors. Each vector can include a raw set of, for example, 2560 data points. In general, each vector can include any number of data points depending on the imaging system. As discussed, high frequency data often includes a large amount of noise, including high frequency and low frequency noise. In some embodiments, the intravascular imaging engine 112 can perform one or more processing functions to effectively reduce the high and/or low frequency noise from the set of image information.

For example, the intravascular imaging engine 112 can perform one or more calculations for reducing noise in the set of image information. In various examples, one or more calculations can include a comparison of two or more data points within the image information. In general, comparisons of data can include any calculation operation that incorporates a value of the one or more data points being compared. Accordingly, comparisons of data points can include combining values associated with the data points, such as summing, averaging, or determining other data set parameters, such as determining a median value, mode, a minimum value, a maximum value, and the like. Comparisons can further include performing mathematical or other functions involving such data, such as grouping or eliminating of data based on compared values, for example.

In some embodiments, the intravascular imaging engine 112 is configured to receive each vector from the raw set of vectors and perform coherence filtering in order to filter out high frequency noise and improve the SNR of the image information. In some examples, the coherence filter is configured to group vectors from the raw set of vectors into raw vector groups of one or more vectors and to generate a first set of vectors based on comparisons of data in each vector in the raw vector groups. In some examples, the first set of vectors is generated based on comparisons of data points of each vector within the raw vector group with one another at like radial positions. That is, vectors can be compared with one another at like vector coordinates during coherence filtering. In some examples, the comparison can include taking an average of the vectors in the raw vector group at like vector coordinates. In various embodiments, the average can be a weighted average or a standard mean calculation. As a result of the coherence filtering, in some embodiments, each vector in the first set of vectors is representative of vectors of one of the raw vector groups and includes a first set of data points having the same number of data points as the raw sets of data points in each vector in the set of raw vectors.

In an exemplary embodiment, each raw vector group consists of two vectors, each having N data points. In such embodiments, the raw set of vectors can include twice as many vectors as the first set of vectors. Accordingly, raw sets of vectors having 4096, 2048, or 1024 vectors can be filtered into first sets of vectors having 2048, 1024, or 512 vectors, respectively.

In general, coherence filtering can include combining one or more vectors in one or more combinations, for example, averaging. In some embodiments, a set of X vectors are simply averaged to create a single, average vector. Averaging can be performed, for example, point-wise among averaged vectors. For instance, in embodiments in which each vector corresponds to an angular coordinate in polar coordinates while each vector entry corresponds to the a different radial position in polar coordinates, comparison of two vectors can be performed at each common radial position (i.e., the nth vector entry of one vector is compared with the nth vector entry in another vector).

In some such embodiments, if the transducer 108 provides M total vectors to the intravascular imaging engine 112, the resultant number of vectors after averaging would be M/X. In more complicated embodiments, various forms of weighted averaging or averaging in multiple combinations can be used. In one specific example, a series of four vectors (v1, v2, v3, v4) can be processed such that four resulting "super vectors" (s1, s2, s3, s4) are created. One such processing example is as follows:

$s1=\Sigma(v2,v3,v4)$ $s2=\Sigma(v1,v3,v4)$ $s3=\Sigma(v1,v2,v4)$ $s4=\Sigma(v1,v2,v3)$ In this example, each possible combination of three unique vectors is used to create a resulting "super vector." In some embodiments, each sum can be scaled to provide a more traditional average.

In the preceding example, four vectors are processed into four new vectors, each effectively comprising an average of three of the original four. The image information that would be present in all four original vectors is preserved in the new vectors, but the noise that would likely be present in less than all four original vectors would be diminished significantly in the new vectors. Accordingly, each of the resulting vectors has reduced high frequency noise, and the resultant number of vectors after averaging is still M. In preferred embodiments, the vectors that are averaged represent image information from overlapping or near overlapping sections of the patient's vasculature. In general, any number of vectors of overlapping sections can be combined to produce resultant "super vectors."

Figure 2A:
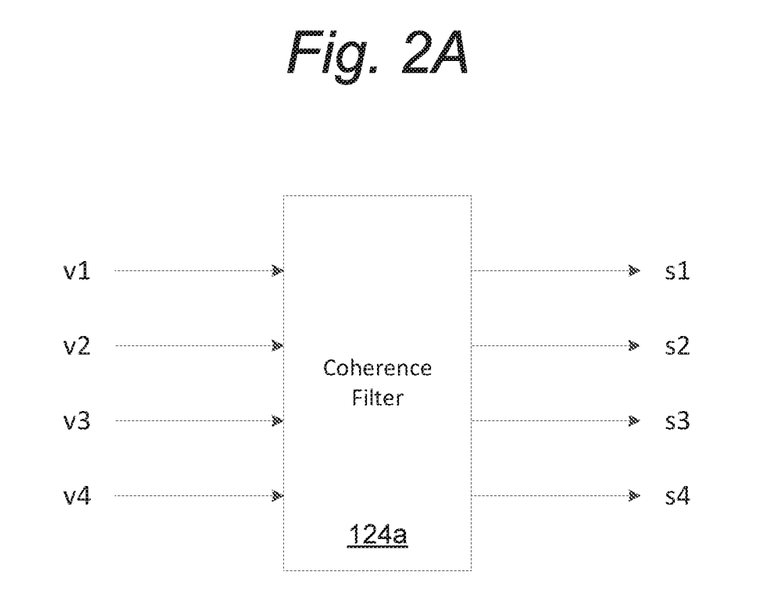
FIGS. 2A and 2B illustrate exemplary coherence filter configurations as part of the intravascular imaging engine.
Figure 2B:
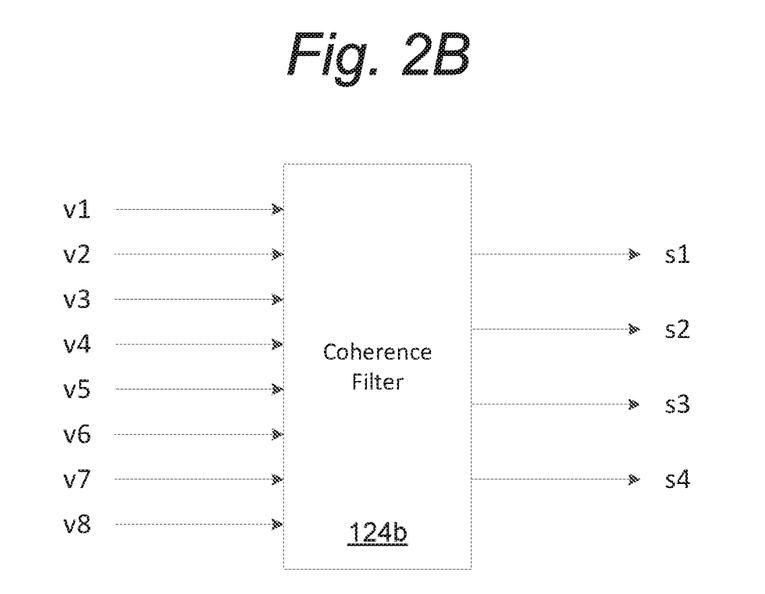

FIGS. 2A and 2B illustrate exemplary coherence filter configurations as part of the intravascular imaging engine. FIG. 2A shows a coherence filter 124a similar to the one described above receiving four vector inputs (v1, v2, v3, and v4) and outputting four "super vectors" (s1, s2, s3, and s4). In some embodiments, the number of resultant "super vectors" is lower than the number of input vectors, such as shown in FIG. 2B. FIG. 2B shows an exemplary coherence filter 124b receiving eight input vectors (v1-v8) and outputting only four "super vectors" (s5-s8). In such embodiments, input vectors can be combined in any way to reduce the total number of resultant "super vectors," such as selecting four possible combinations of two or more input vectors each and performing an averaging function. Many implementations are possible and are within the scope of the coherence filter described in this disclosure. The coherence filter can be configured to output "super vectors" having lower high frequency noise and a higher SNR than the high frequency input vectors produced by the high frequency image information received from the transducer 108.

Referring again to FIG. 1, in some embodiments, vectors can be processed by the intravascular imaging engine 112 using an envelope detection module comprising one or more envelope detector. The envelope detection module can be configured to receive the first set of vectors from the coherence filter and generate a second set of vectors based on comparisons of data points within each first set of data points with one another. That is, in some examples, the envelope detection module generates a second set of vectors based on comparisons of data points within each vector of the first set of vectors. The envelope detection module can act on each of the first set of vectors independently. Accordingly, in some embodiments, the second set of vectors comprises the same number of vectors as the first set of vectors. The envelope detection module can include a plurality of envelope detectors arranged in parallel for parallel processing of vectors in the first set of vectors. The parallel envelope detectors can be arranged such that each envelope detector is configured to generate a subset of the second set of vectors.

Figure 3:
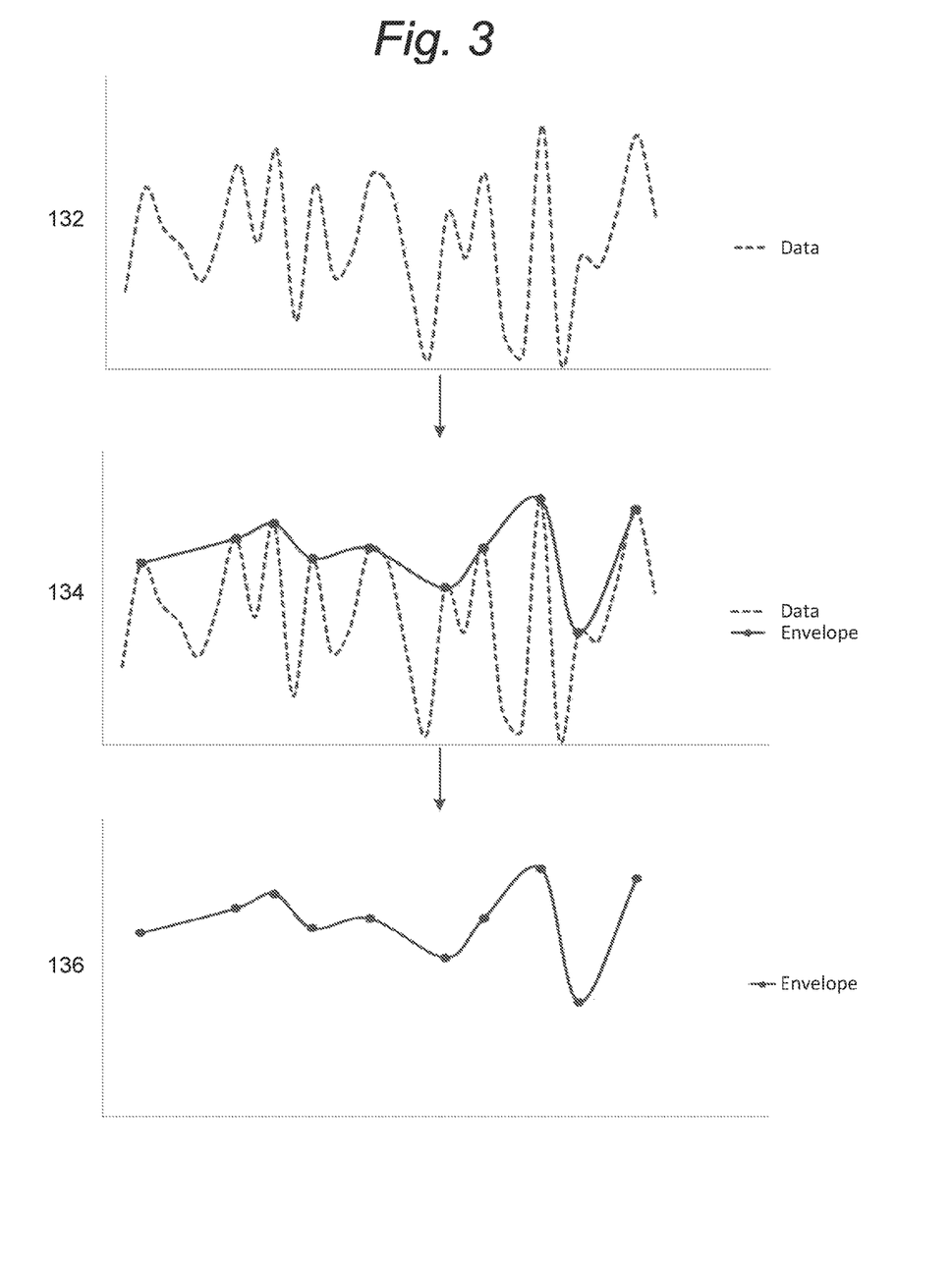
FIG. 3 shows an exemplary envelope detection process.

In some examples, an envelope detector in the envelope detection module can effectively convert vectors comprising high frequency data into vectors comprising low frequency data, while maintaining the general shape of the waveform represented by the vector. FIG. 3 is an illustrative envelope detection process. FIG. 3 shows a set of high frequency data in frame 132 to be input into the envelope detector. Peaks in the data are detected to create an (upper) envelope of the data in frame 134. Other envelope functions are also possible. The envelope is output as the signal shown in frame 136, having the same general wave shape as the input data with a lower frequency. In some examples, "super vectors" created from the received image information and having reduced high frequency noise can be directed to one or more envelope detectors. In some embodiments, a plurality of parallel envelope detectors can be used. For example, in an embodiment in which X vectors are processed to create Y "super vectors," the system 100 can include Y envelope detectors in parallel to process each of the "super vectors" simultaneously. In the exemplary case presented above, four parallel envelope detectors can be used to process "super vectors" s1-s4 or s5-s8 simultaneously. In such an example, processing time for performing envelope detection is reduced by a factor of four when compared to systems using a single envelope detector.

In embodiments in which the system is configured to display an image representative of the received image information, high frequency vectors can comprise too much data for effective display. The envelope detectors can generally output vectors comprising low frequency brightness data representative of the received information even when the input "super vectors" are high frequency vectors. In this way, envelope detectors can be used to smooth the data and make it suitable for display in the form of low frequency vectors of brightness data.

The low frequency brightness data can be in the form of a series of vectors, each vector comprising a series of data points. The vectors can make up the second set of vectors and the series of data points in each vector can include the second set of data points in each of the vectors. In some embodiments, each vector generally corresponds to an orientation angle of the transducer within the patient, while the data within each vector generally corresponds to information of the patient's vascular structure encompassed within the angular range of the vector at increasing radial distances from the transducer. As noted, because of the angular width of the wave-based energy emitted by the transducer, imaged angular sections represented by differing vectors can overlap one another.

Figure 4A:
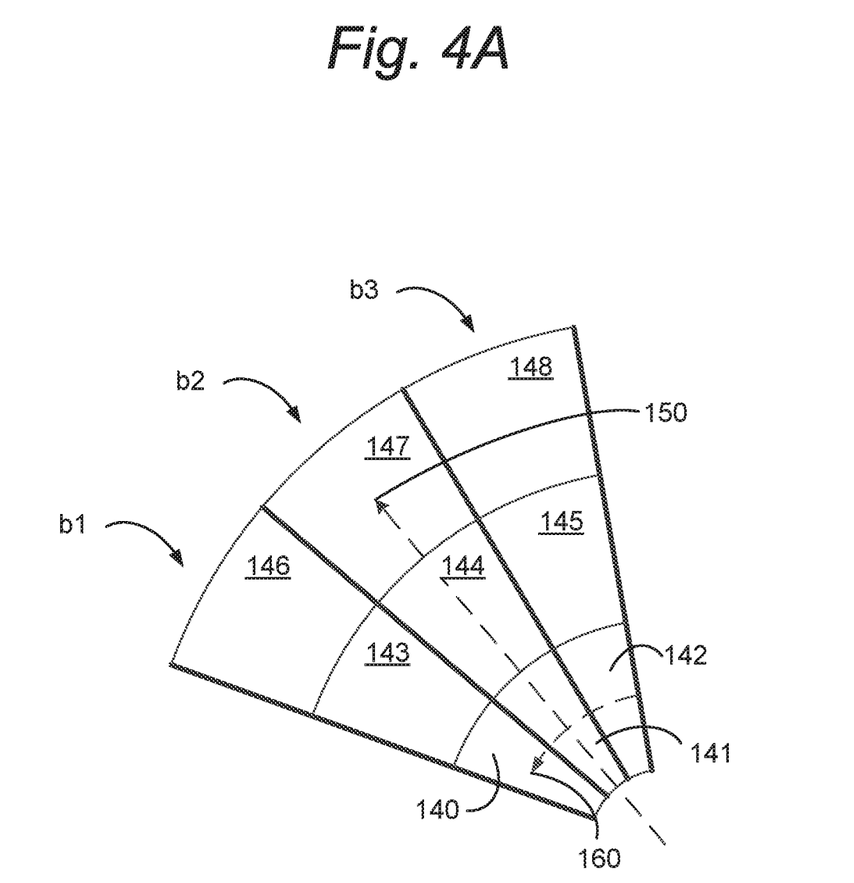
FIG. 4A-4B show exemplary sets of brightness data arranged for processing or display.

FIG. 4A shows an exemplary set of brightness data arranged for display. In this example, brightness data is arranged in polar coordinates, with data points 140-148 divided both angularly and radially. Each angular section separated by bold lines represents a vector of brightness data, corresponding to an orientation of the transducer 108 during image information acquisition. Each point within an angular section represents a data point within that vector. For example, in the embodiment shown, brightness vector b1 comprises data points 140, 143 and 146; brightness vector b2 comprises data points 141, 144, and 147; and brightness vector b3 comprises data points 142, 145, and 148.

As discussed, vectors can represent a range of angles to as to generally comprise data representative of an angular section of a patient's vascular structure. Accordingly, nearby vectors can comprise data representing overlapping sections of vascular structure. A sufficient number of vectors can effectively represent a full 360° image of the vascular structure. The number sufficient depends on the angular width subtended by each vector and the amount of overlap of each vector. Vectors and the data points they comprise can, for instance, make up a polar coordinate representation of the imaged vascular structure, with the vector in which a data point is contained corresponding to the angle coordinate of that point, and the location of the data point within the vector corresponding to the radial position of that point.

Vectors comprising low frequency brightness data can be used to generate a display representative of the image information received by the catheter assembly. The display can be displayed in color, black and white, grayscale, or any other desired color palette, and can comprise a set of pixels, each pixel representing a data point of brightness data. The brightness and/or color of each pixel can directly correspond to the brightness data represented in the corresponding data point. In some embodiments, even if high frequency noise has been reduced from the image information such as described with regard to coherence filtering, the low frequency brightness data used to generate the display can contain low frequency noise.

In some embodiments, the intravascular imaging engine can be configured to process and combine the low frequency brightness data in order to reduce the low frequency noise. Such processing can include one or both of filtering and averaging. In some examples, the system can include a spatial filter configured to receive data from the envelope detection module for further processing. The spatial filter can be configured to group vectors of the second set of vectors into processed vector groups. Each of the processed vector groups can include any number of vectors from the second set of vectors.

The spatial filter can be configured to generate an enhanced set of vectors based on data in the second set of vectors. For instance, in some examples, the spatial filter can perform comparisons of data points of each processed vector group's vectors. The comparisons can be performed, for example, at like and near radial positions among the vectors in each processed vector group. Each vector in the resulting enhanced set of vectors can be representative of the vectors in one of the processed vector groups. Each vector in the enhanced set of vectors can include an enhanced set of data points. In some examples, the enhanced set of data points in each vector in the enhanced set of vectors can have as many data points as the second set of data in each vector in the second set of vectors.

In some systems, processing the second set of vectors via the spatial filter can include spatial filtering of brightness data. Examples of spatial filtering can include averaging data points with a set of spatially proximate additional data points. Spatially proximate data points can be data points whose polar coordinate representation are within some predetermined distance of one another. In a 360° image representation, averaged points can include, for example, all data points within a certain spatial distance of a certain point—a technique called proximal averaging. With reference to FIG. 4A, for example, point 144 can be processed to be averaged with each neighboring points 140-148. In various embodiments, the spatial requirement used to define the averaging process can be predetermined or set by a user.

Another example of spatial filtering can comprise averaging all data points within a certain spatial distance of a certain point and within the same vector as the certain point—a technique called radial averaging. For example, points 140, 141 and 142 can be averaged along line 160 to generate spatially filtered data at 141. Yet another spatial filtering example can comprise averaging all data points within a certain distance of a certain point and having the same radial position within their corresponding vector—a technique called angular averaging. For example, points 141, 144 and 147 can be averaged along line 150 to generate spatially filtered data at 144. Spatial filtering can involve a median filter, which can be useful for minimizing the impact of outliers.

In general, spatial filtering can include averaging or other methods of combining data chosen via any other selection of proximate data points. Spatial filtering can include removing outliers from a set of data prior to averaging the remaining set of data. In some embodiments, filtering operations can be determined on a point-by-point basis. For example, not all data points will necessarily have the same number of surrounding data points within a given spatial dimension. Spatially filtering the low frequency brightness data can act to reduce the low frequency noise contained therein, effectively raising the SNR.

Figure 4B:
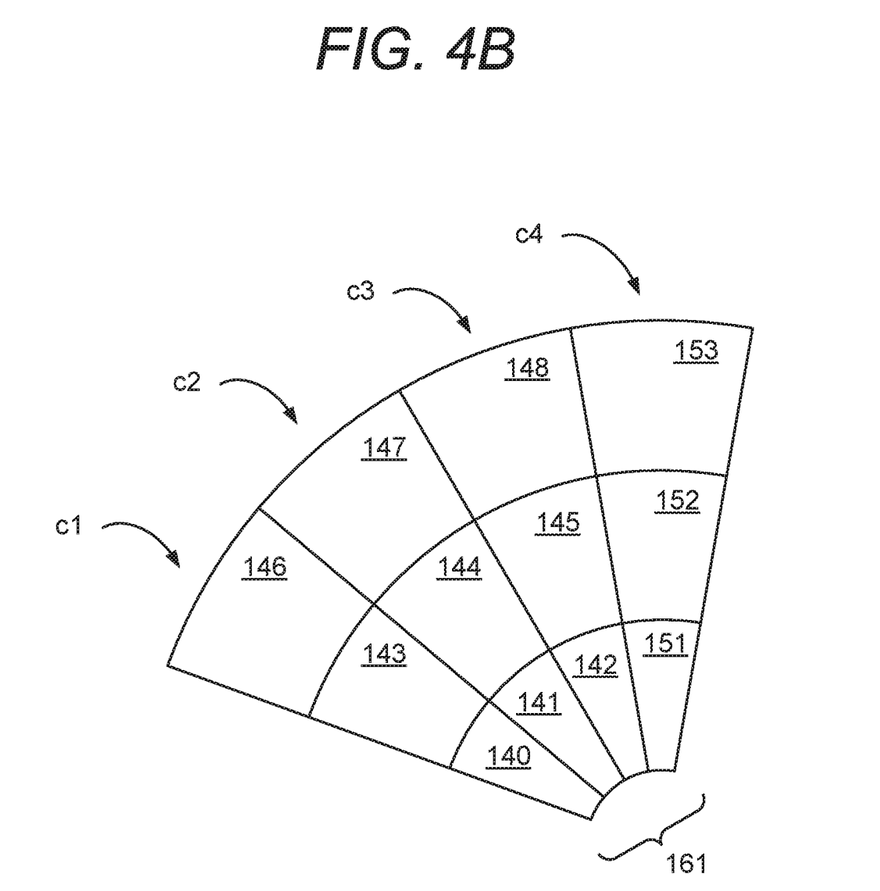

Still another example of spatial filtering can be described with regard to FIG. 4B. FIG. 4B is an exemplary subset of image information data, in which 4 vectors $c1$, $c2$, $c3$ and $c4$ each include three data points. Each vector ($c1$-$c4$) corresponds to an angular coordinate while each data point within each vector corresponds to a radial position in a polar coordinate representation. In some examples in accordance with FIG. 4B, vectors $c1$-$c4$ are vectors in the second set of vectors resulting from an envelope detection step. In an exemplary spatial filtering step, vectors $c1$-$c4$ can be grouped into a processed vector group 161 by the spatial filter. The processed vector group can in general include any appropriate number of vectors from the second set of vectors, and generally includes a plurality of vectors. In the illustrated embodiment of FIG. 4B, the processed vector group 161 comprises four vectors ($c1$-$c4$). The spatial filter can generate an enhanced set of vectors based on comparisons of data points in the vectors within each processed vector group, such as $c1$-$c4$.

In an exemplary process, the spatial filter can generate the enhanced set of vectors based on comparisons of data points of each processed vector group's vectors with one another at like and near radial positions (e.g., radial positions including points 140, 143, and 146 in FIGS. 4A and 4B). In some instances, each vector in the enhanced set of vectors is representative of the vectors of one of the processed vector groups. With regard to FIG. 4, processed vector group 161 can be used to generate a vector in the enhanced set of vectors. In an exemplary method, points at a first radial position (e.g., points 143, 144, 145, 152) are analyzed, and the data point with the highest value is excluded from the analysis. Then points with neighboring radial positions (e.g., points 140, 141, 142 and 151, and points 146, 147, 148, 153) are similarly analyzed, and the highest value data point at each radial position is excluded. In accordance with the illustrated embodiment, of the 12 data points (140-148, 151-153), three are excluded for being the highest value data point at each radial distance. The remaining nine data points can be compared to generate a data point entry for the first radial position in the resulting enhanced vector. For example, the median value of the remaining nine data points can be used as the corresponding data point at the first radial position in the resulting enhanced vector. A similar analysis can be performed at each radial position of the vectors in the second set of vectors, and accordingly, each vector in the enhanced set of vectors can include an enhanced set of data points having the same number of data points as the second set of data points (i.e., the number of data points in each vector in the second set of vectors).

Figure 5:
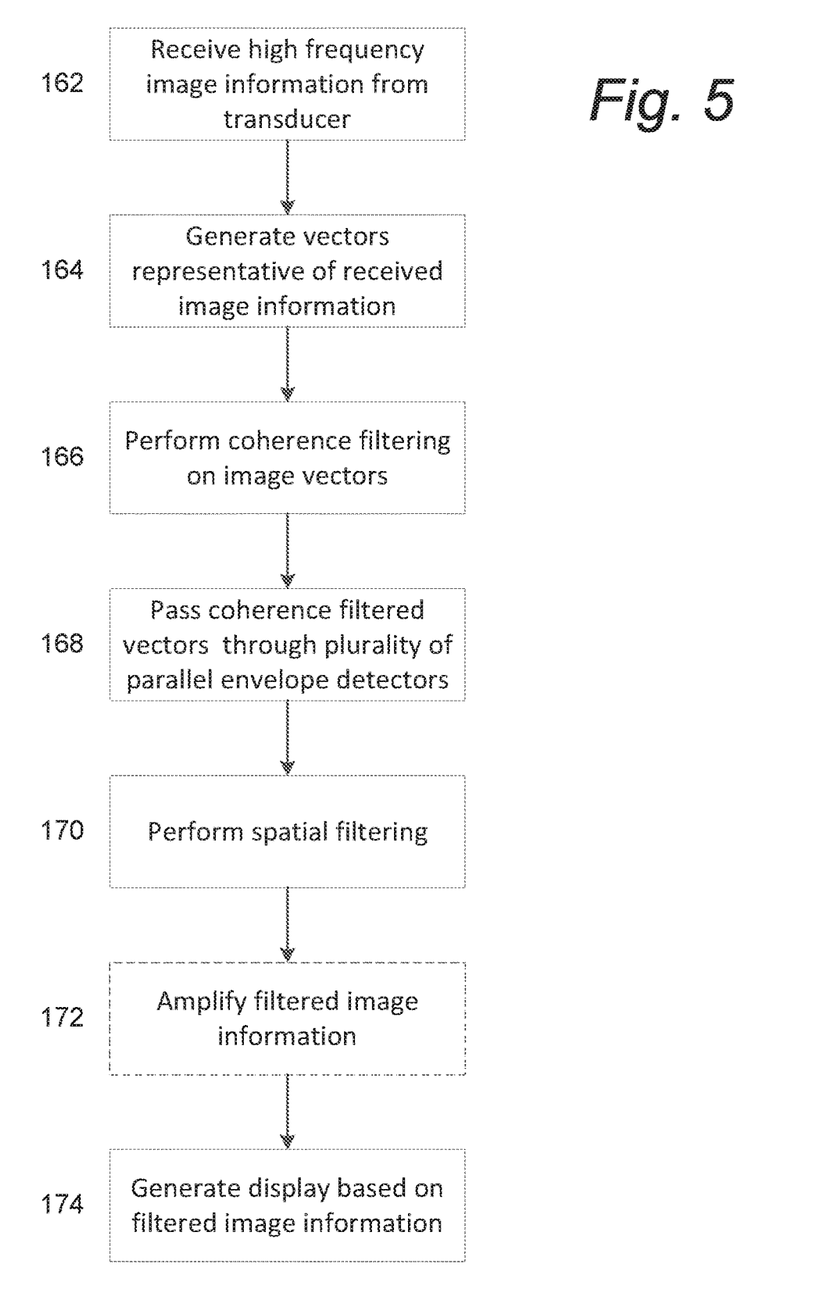
FIG. 5 is a process flow diagram illustrating a multi-step process to generate high resolution intravascular images.

Various processes have been described in which high frequency noise is reduced, high frequency data is converted to low frequency data, and low frequency noise is reduced. In some embodiments, these steps can be aggregated into a multi-step process in order to produce a high resolution intravascular image. FIG. 5 is a process flow diagram illustrating a multi-step process to generate high resolution intravascular images. In an exemplary embodiment, intravascular imaging engine can receive high frequency image information from the transducer 162. In some embodiments, image information is in the form of a series of vectors. In other embodiments, the intravascular imaging engine can generate vectors representative of the received image information 164. Vector generation can comprise digitizing received analog image information from the transducer. In some embodiments, the high frequency image information can comprise raw radio frequency (RF) image information. The intravascular imaging engine can process the received high frequency image information using coherence filtering 166 (e.g., a form of averaging) to reduce the high frequency noise. The coherence filtering process can produce a series of high frequency "super vectors" representing the image information received from the transducer having reduced high frequency noise.

The "super vectors" can be passed through a plurality of envelope detectors arranged in parallel 168 and configured to simultaneously process an equal plurality of "super vectors." The envelope detectors can convert the high frequency "super vectors" into low frequency brightness vectors comprising brightness data representative of the image information received from the transducer. The brightness vectors can represent image information, for example, in polar coordinates, with each data point of each vector representing an angular and radial component.

Data from the brightness vectors can be subject to spatial filtering 170, including, for example, proximal, angular, or radial averaging, in order to reduce the low frequency noise in the low frequency brightness data. The intravascular imaging engine can include an image generator configured to generate an image representing the image information received from the transducer 174. The image generator can be configured to generate an image based on an enhanced frame of imaging information, the enhanced frame including data from each vector in the enhanced set of vectors.

Methods that include coherence filtering, envelope detection, and spatial filtering, can process raw high frequency image information received from the transducer into low frequency brightness data in which both high frequency and low frequency noise has been significantly reduced. Such methods can effectively reduce a full frequency range of image noise, with the frequency ranges affected by the high and low frequency noise reduction overlapping at least partially. Such noise reduction can significantly improve the SNR of the image information.

As noted, in many embodiments, the intravascular imaging system includes a display coupled to the imaging engine and configured to display the image generated by the image generator. Accordingly, in some embodiments, the spatially filtered brightness data can be displayed as an intravascular image on the display. As discussed herein, image information acquired at high frequencies tends to be less intense than that acquired at lower frequencies, and therefore may be difficult to observe in full detail on the display. However, because the processing steps prior to display have effectively reduced both the high and low frequency noise and significantly improved the SNR, gain can be applied to amplify the spatially filtered brightness data 172 for display without also amplifying noise so much as to obscure the image. Accordingly, such a system can take advantage of the high resolution obtainable by high frequency imaging while overcoming the drawbacks that are often associated with it.

In some systems, subsequent processing steps may be performed after spatially filtering the brightness data and prior to display. For example, gamma filtering may be employed to convert the data to the display ability of a monitor (if it is not already within the display ability) and determine an appropriate level of contrast to incorporate into the final image. In some embodiments, gamma filtering can help match the detection ability of the human eye, given that monitors can display a wider range of brightness/colors than the eye can distinguish. Temporal frame filtering (TFF) can be employed, in which a series of images of substantially the same location are processed in order to smooth image regions showing relatively stable tissue features from frame to frame (e.g., vessel wall, lumen blood) and to maintain (not filter) information in image regions where tissue features vary from frame to frame (e.g., lumen border position changes). In many instances, TFF can perform local filtering rather than the same filtering across the entire frame. Scan conversion can be employed in some instances. Scan conversion involves converting from polar coordinates to Cartesian coordinates. The data can be stored in a format that is independent of the anatomy of the vessel (e.g., data is independent of the rotation angle of transducer). This can be called polar format (r-theta). The data can be mapped to the anatomy by scan conversion.

Figure 6:
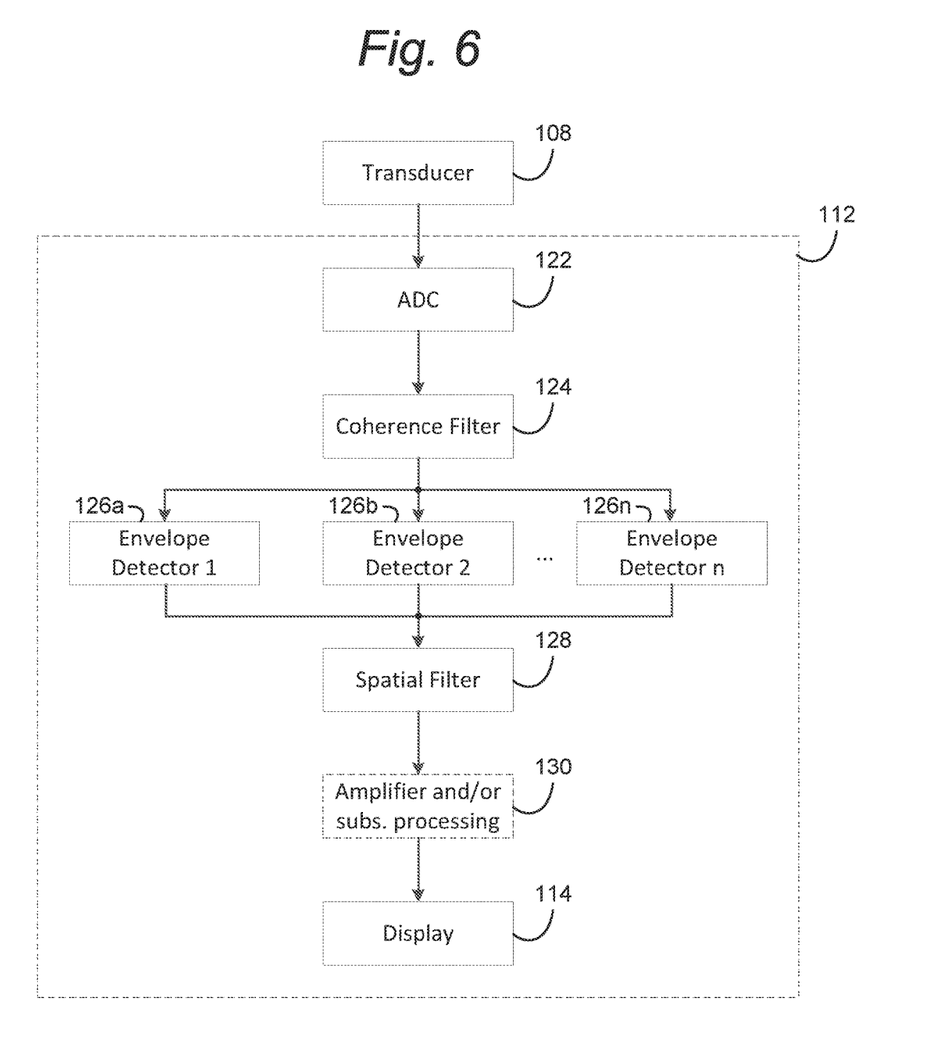
FIG. 6 is a system level block diagram illustrating the flow of image information from the transducer to a display.

FIG. 6 is an illustrative system level block diagram illustrating the flow of image information from the transducer 108 to a display 114. The transducer 108 can emit and receive energy within a patient's vasculature and can transmit high resolution and high frequency image information to the intravascular imaging engine 112 based on the received energy. In some embodiments, the signals comprise analog signals. In such embodiments, the analog signals can be passed through an analog-to-digital converter (ADC) 122 to digitize the data into image information vectors. Resulting image information vectors can be in the form of a raw set of vectors, which can be passed through a coherence filter 124, which can reduce the amount of high frequency noise in the image information and produce a first set of vectors. In some instances, the first set of vectors can be designated as "super vectors," and can include the same number of data points as associated vectors from the raw set of vectors. In some examples, the raw set of vectors consists of 4096 vectors, which are processed into 2048 "super vectors," such that the first set of vectors consists of 2048 vectors.

"Super vectors" from the first set of vectors can be sent from the coherence filter 124 to a plurality of envelope detectors 126a, 126b ... 126n arranged in parallel to process the "super vectors" to generate a second set of vectors, which can be considered low frequency brightness vectors. In some examples, low frequency brightness vectors in the second set of vectors include fewer data points than the associated "super vectors" from the first set of vectors. In some examples, the reduction in the number of data points between the super vectors and the low frequency brightness vectors can be by a factor of five, ten, or other appropriate scaling factor so that each vector in the second set of vectors provides an accurate low-frequency representation of corresponding vectors in the first set of vectors. In some examples, the second set of vectors can include the same number of low frequency brightness vectors as the first set of vectors includes "super vectors."

The brightness vectors in the second set of vectors may be passed to a spatial filter 128 configured to reduce the amount of low frequency noise from the brightness vectors. The spatial filter 128 can group the brightness vectors from the second set of vectors into processed vector groups. Data within the processed vector groups can be compared in the spatial filter 128 to generate an enhanced set of vectors, each including enhanced set of data points. Spatially filtered brightness vectors in the enhanced set of vectors can include the same number of data points as the low frequency brightness vectors in the second set of vectors. In some examples, the spatial filter 128 can reduce the number of vectors. For instance, the spatial filter 128 can reduce the number of vectors in the second set of vectors by a factor of four in generating the enhanced set of vectors. That is, the enhanced set of vectors at the output of the spatial filter 128 can include one fourth as many vectors as the second set of vectors input into the spatial filter 128. The enhanced set of vectors can collectively be combined to form an enhanced frame of imaging data.

The resulting spatially filtered brightness vectors in the enhanced set of vectors can be passed to an amplifier and/or subsequent processing components 130 such as gamma filtering or temporal frame filtering to ready the data for display. Components 130 can include an image generator for generating an image based on the enhanced frame of imaging data. The generated image can be sent to display 114 for real-time display of a patient's vascular structure with reduced high and low frequency noise.

As described, exemplary intravascular imaging systems can include an intravascular imaging engine 112 configured to receive image information from a transducer 108 within a catheter assembly 102. The image information can be processed and displayed on a display 114. In many systems, the transducer 108 is configured to move longitudinally within the patient in order to image multiple locations. As such, it can be advantageous to generate a real-time display so that a user of the intravascular imaging system can observe the vascular structure as the transducer 108 moves through the patient. The processing steps as described herein can be performed in such a way so that high resolution images generated from high frequency image information acquisition can be displayed real-time at a constant frame rate. In some embodiments, the frame rate can range from 30 to 60 frames per second. In some embodiments, the frame rate can be up to 160 frames per second.

In some intravascular imaging systems, a user can initiate any of the processing procedures described herein via the user interface 120. A system operator can, for example, initiate high resolution, high frequency imaging via the user interface 120 and observe real-time high resolution in vivo image information of a patient's vascular structure. The system operator can use this received information to translate the transducer 108 within the patient in a desired direction via the user interface 120 while continuing to observe the imaged structure. Processes herein described may be encoded in non-transitory computer-readable medium containing executable instructions for causing a processor to carry out such processes. Non-transitory computer-readable medium can be included in memory in the intravascular imaging engine 112.

Various examples of systems and methods for intravascular imaging have been described. It will be appreciated that these and others are within the scope of the invention.

The invention claimed is:

1. A system for producing high definition intravascular images comprising:
    an intravascular imaging catheter assembly configured to generate a raw frame of imaging information that includes a raw set of vectors, with each vector of the raw set of vectors comprising a raw set of data points;
    an imaging engine coupled to the intravascular imaging catheter assembly and being configured to receive the raw frame of imaging information from the intravascular imaging catheter assembly and to produce an enhanced frame of imaging information that includes an enhanced set of vectors, the imaging engine comprising:
        (a) a coherence filter configured to
            (i) group vectors of the raw set of vectors into raw vector groups and
            (ii) generate a first set of vectors based on comparisons of data points of each raw vector group's vectors with one another, wherein each vector of the first set of vectors
                (A) is representative of the vectors of one of the raw vector groups and
                (B) comprises a first set of data points, and wherein
                generating the first set of vectors comprises generating, for each of the raw vector groups, two or more super vectors within the first set of vectors and associated with the raw vector group such that the first set of vectors consists of the generated super vectors,
        (b) an envelope detection module comprising a plurality of envelope detectors arranged in parallel and configured to generate a second set of vectors based on comparisons of data points within each of the first set of data points with one another, wherein (i) each vector of the second set of vectors comprises a second set of data points with a smaller number of data points that are representative of the data points of the first set of data points and (ii) the second set of vectors comprises the same number of vectors as the first set of vectors,
        (c) a spatial filter configured to (i) group vectors of the second set of vectors into processed vector groups and (ii) generate the enhanced set of vectors based on comparisons of data points of each processed vector group's vectors with one another, wherein each vector of the enhanced set of vectors (A) is representative of the vectors of one of the processed vector groups and (B) comprises an enhanced set of data points, and
        (d) an image generator configured to generate an image based on the enhanced frame of imaging information; and
    a display coupled to the imaging engine and configured to display the image generated by the image generator.

2. The system of claim 1, wherein the coherence filter generates the first set of vectors based on comparisons of data points of each raw vector group's vectors with one another at like radial positions.

3. The system of claim 1, wherein the spatial filter is configured to generate the enhanced set of vectors based on comparisons of data points of each processed vector group's vectors with one another at like and near radial positions.

4. The system of claim 1, wherein the enhanced set of data points has the same number of data points as the second set of data points.

5. The system of claim 1, wherein the system is an intravascular ultrasound (IVUS) system.

6. An imaging engine configured to receive raw frames of imaging information from an intravascular imaging catheter assembly and to produce an enhanced frame of imaging information that includes an enhanced set of vectors, the imaging engine comprising:
(a) a coherence filter configured to
(i) group vectors of a raw set of vectors into raw vector groups, and
(ii) generate a first set of vectors based on comparisons of data points of each raw vector group's vectors with one another, wherein each vector of the first set of vectors
(A) is representative of the vectors of one of the raw vector groups and
(B) comprises a first set of data points, and
wherein generating the first set of vectors comprises generating, for each of the raw vector groups, two or more super vectors within the first set of vectors and associated with the raw vector group such that the first set of vectors consists of the generated super vectors;
(b) an envelope detection module comprising a plurality of envelope detectors arranged in parallel and configured to generate a second set of vectors based on comparisons of data points within each of the first set of data points with one another, wherein (i) each vector of the second set of vectors comprises a second set of data points with a smaller number of data points that are representative of the data points of the first set of data points and (ii) the second set of vectors comprises the same number of vectors as the first set of vectors;
(c) a spatial filter configured to (i) group vectors of the second set of vectors into processed vector groups and (ii) generate the enhanced set of vectors based on comparisons of data points of each processed vector group's vectors with one another, wherein each vector of the enhanced set of vectors (A) is representative of the vectors of one of the processed vector groups and (B) comprises an enhanced set of data points; and
(d) an image generator configured to generate an image based on the enhanced frame of imaging information.

7. The imaging engine of claim 6, wherein the coherence filter generates the first set of vectors based on comparisons of data points of each raw vector group's vectors with one another at like radial positions.

8. The imaging engine of claim 6, wherein the enhanced set of data points has the same number of data points as the second set of data points.

9. The imaging engine of claim 6, wherein the image generated by the image generator is a high definition intravascular image generated and displayed in real time.

10. The imaging engine of claim 6, wherein the envelope detection module comprises multiple envelope detectors arranged in parallel, with each envelope detector being configured to generate a subset of the second set of vectors.

11. The imaging engine of claim 6, wherein the coherence filter is configured to generate the first set of vectors based on comparisons of data points of each raw vector group's vectors with one another at like radial positions.

12. The imaging engine of claim 6, wherein the spatial filter is configured to generate the enhanced set of vectors based on comparisons of data points of each processed vector group's vectors with one another at like and near radial positions.

13. A method for filtering and processing raw high frequency image information into low frequency brightness data, the method comprising:
receiving raw frames of imaging information from an intravascular imaging catheter assembly, the raw frames of imaging information including a raw set of vectors, with each vector of the raw set of vectors comprising a raw set of data points;
removing high frequency noise from the raw frames of imaging information by (i) grouping vectors of the raw set of vectors into raw vector groups and (ii) generating a first set of vectors based on comparisons of data points of each raw vector group's vectors with one another, wherein each vector of the first set of vectors
(A) is representative of the vectors of one of the raw vector groups and (B) comprises a first set of data points having the same number of data points as the raw set of data points; and wherein
generating the first set of vectors comprises generating, for each of the raw vector group, two or more super vectors within the first set of vectors and associated with the raw vector group such that the first set of vectors consists of the generated super vectors;
converting high frequency data into low frequency brightness data by generating a second set of vectors based on comparisons of data points within each of the first set of data points with one another, wherein (i) each vector of the second set of vectors comprises a second set of data points with a smaller number of data points that are representative of the data points of the first set of data points and (ii) the second set of vectors comprises the same number of vectors as the first set of vectors;
removing low frequency noise by (i) grouping vectors of the second set of vectors into processed vector groups and (ii) generating an enhanced set of vectors based on comparisons of data points of each processed vector group's vectors with one another, wherein each vector of the enhanced set of vectors (A) is representative of the vectors of one of the processed vector groups and (B) comprises an enhanced set of data points; and
providing the enhanced set of vectors as an enhanced frame of imaging information to an image generator for generating an image.

14. The method of claim 13, further comprising generating the image with the image generator and amplifying the image.

15. The method of claim 13, further comprising generating the image with the image generator and applying gain to the image.

16. The method of claim 13, wherein the method reduces a full frequency range of image noise including high and low frequency noise and wherein frequency ranges affected by high and low frequency noise reduction overlap at least partially.

17. The method of claim 13, wherein removing high frequency noise from the raw frames of imaging information by generating the first set of vectors is based on comparisons of data points of each raw vector group's vectors with one another at like radial positions.

18. The method of claim 17, wherein generating the enhanced set of vectors is based on comparisons of data points of each processed vector group's vectors with one another like and near radial positions.

19. The method of claim 13, wherein the comparisons of data points of each processed group's vectors with one another at like and near radial positions exclude outlier data points at like and near radial positions.

20. The method of claim 13, wherein the enhanced set of data points has the same number of data points as the second set of data points.

* * * * *